United States Patent [19]
Kelly et al.

[11] Patent Number: 5,383,919
[45] Date of Patent: Jan. 24, 1995

[54] THERMAL THERAPY PAD

[75] Inventors: Kevin A. Kelly, Galloway; Roman Szpur, Kettering, both of Ohio

[73] Assignee: Danninger Medical Technology, Inc., Columbus, Ohio

[21] Appl. No.: 63,240

[22] Filed: May 18, 1993

[51] Int. Cl.$^6$ .................................... A61F 7/00
[52] U.S. Cl. ...................... 607/104; 607/114; 601/15
[58] Field of Search ............. 607/96, 104, 108, 109, 607/111, 114; 128/24 R; 602/2, 14; 62/259.3; 601/15

[56] References Cited

U.S. PATENT DOCUMENTS

| | | | |
|---|---|---|---|
| 396,208 | 1/1889 | Herndon | 165/46 |
| 735,876 | 8/1903 | Holland | 383/119 |
| 3,112,792 | 12/1963 | Coleman, Jr. et al. | |
| 3,867,939 | 2/1975 | Moore et al. | |
| 3,894,213 | 7/1975 | Agarwala | |
| 4,149,541 | 4/1979 | Gammons et al. | 607/104 |
| 4,253,449 | 3/1981 | Arkans et al. | 128/24 R |
| 4,561,441 | 12/1985 | Kolodziej | 607/114 |
| 4,821,354 | 4/1989 | Little | 607/104 |
| 4,979,375 | 12/1990 | Nathan et al. | 607/104 |
| 5,125,238 | 6/1992 | Ragan et al. | |

FOREIGN PATENT DOCUMENTS 8503216 8/1985 WIPO ................. 607/104

OTHER PUBLICATIONS

A brochure entitled "Dual-Temp TM System Specifications" by Seabrook Medical Systems, Inc., 673 Wilmer Avenue, Cincinnati, Ohio 45226-1859.
A brochure entitled "Polar Care Cold Therapy" by Breg, 1281 Liberty Way, Vista, Calif. 92083.
A brochure by InCare Medical Products, Div. of Hollister Inc., 2000 Hollister Drive, Libertyville, Ill. 60048.

*Primary Examiner*—Richard J. Apley
*Assistant Examiner*—Jeanne M. Mollo
*Attorney, Agent, or Firm*—Hudak & Shunk Co.

[57] ABSTRACT

A device is provided to enable simultaneous application of continuous passive motion therapy and thermal therapy. The device specifically provides an improved fluid transfer pad having a first membrane in a sealed cooperation with a second membrane to form a fluid receiving cavity, and the device having a fluid conduit means comprising an inlet conduit and an outlet conduit. The device further includes an internal reinforcement which telescopes within the fluid inlet conduit and extends beyond the inlet conduit into the fluid containing cavity. The internal reinforcement is lobed to form open flow surfaces or alternatively, is a spiral cut tube which allows an enlarged area of fluid diffusion.

3 Claims, 2 Drawing Sheets

THERMAL THERAPY PAD

FIELD OF INVENTION

The invention relates generally to a thermal transfer pad such as a heating pad or cooling pad, used generally in the application of thermal therapy. In particular, a pad is provided having increased reliability inasmuch as the pad has improved continuity of flow.

BACKGROUND

It has long been known that the application of heat or cold to an injury can influence blood circulation at an injured site, decrease swelling, and increase the comfort of the patient. In the past, such treatment included the use of hot water bottles and ice packs. More recently, however, such treatment has evolved into a therapy using a fluid, such as water, as a thermal transfer media. The fluid is heated or cooled by appropriate means within a housing, and pumped through a conduit, to a pad, which is in contact to the injured portion of the user. Sometimes during the course of using a thermal therapy device, the flow of the fluid will be blocked. Flow blockage occurs, for example, when the pad becomes tangled in the bedclothes or if the patient is improperly positioned on the pad. It is typical for flow blockage to be a problem at the fluid inlet to the pad.

While it has been proposed to solve flow problems through the use of a higher pressure pump, this also can be a problem. A higher pressure pump may cause problems such as ballooning of the pad or rupture of the pad membrane. Moreover, it is not practically possible to increase the pressure to overcome crimping or flow restrictions and provide for continuity of flow. These problems result from the characteristics of the pad material, for example, it is desirable that the pad material is thin in order to maximize heat transfer characteristics. In addition, the pad material should be flexible in order to maximize the contact with the patient through a variety of positions. Notwithstanding the fact that the membrane is thin and flexible, it is best to provide for low probability of leakage for reasons of patient safety. Therefore, the fluid pressure in the pad should be below 20 psi, and most preferably below about 10 psi.

It is desirable to combine thermal therapy with other therapies, such as continuous passive motion which involves the passive flexion and extension of an injured joint. While a combination of these therapies may be of great medical benefit to the patient, there are certain mechanical difficulties in combining these therapies. Most notably, the prior art thermal transfer pads present problems with blockage to fluid flow. Obstructions to fluid flow are a problem if, for example, a thermal transfer pad is applied when the patient is bandaged in the operating room, and in particular if the patient is subsequently subjected to CPM therapy. The prior art pads have had a tendency to crimp at the joint between the fluid transfer conduit and the pad. One prior art solution to this problem, is an alternative circuit from the inlet conduit to the outlet conduit of the pad. While this solution maintains the fluid flow through the housing, it obviates the therapy, since it inhibits the application of heat or cold to the patient through the pad.

It is therefore an object of the present invention to provide a thermal therapy pad which is suitable for use in the application of thermal therapy, in conjunction with continuous passive motion therapy. This pad is unique in that it has a soft flexible inlet reinforcement. This inlet reinforcement specifically consists of a soft flexible fluid inlet having a flow opening with an increased area through which the fluid diffuses into the pad. It is advantageous if the fluid outlet is similarly reinforced.

The pad of the present invention has increased reliability inhibiting flow obstruction, and the reliability results from a increased area of diffusion in the pad inlet as well as from inlet reinforcement.

In a preferred embodiment of the present invention, the increased area of diffusion is provided by a double conduit construction. A soft flexible inner flow surface, or conduit, is provided, which assures that the inlet remains an open conduit by providing alternate escape paths for the transfer fluid. In a most preferred embodiment, the inner flow surface is provided by a spiral cut inlet reinforcement which extends from the inlet conduit into the body of the thermal transfer pad.

BRIEF DESCRIPTION OF DRAWINGS

FIGS. 5A–5E are transverse cross-sectional views of alternative embodiments for reinforcement conduits which may be applied to the invention.

DETAILED DESCRIPTION OF THE INVENTION

Figure 1:
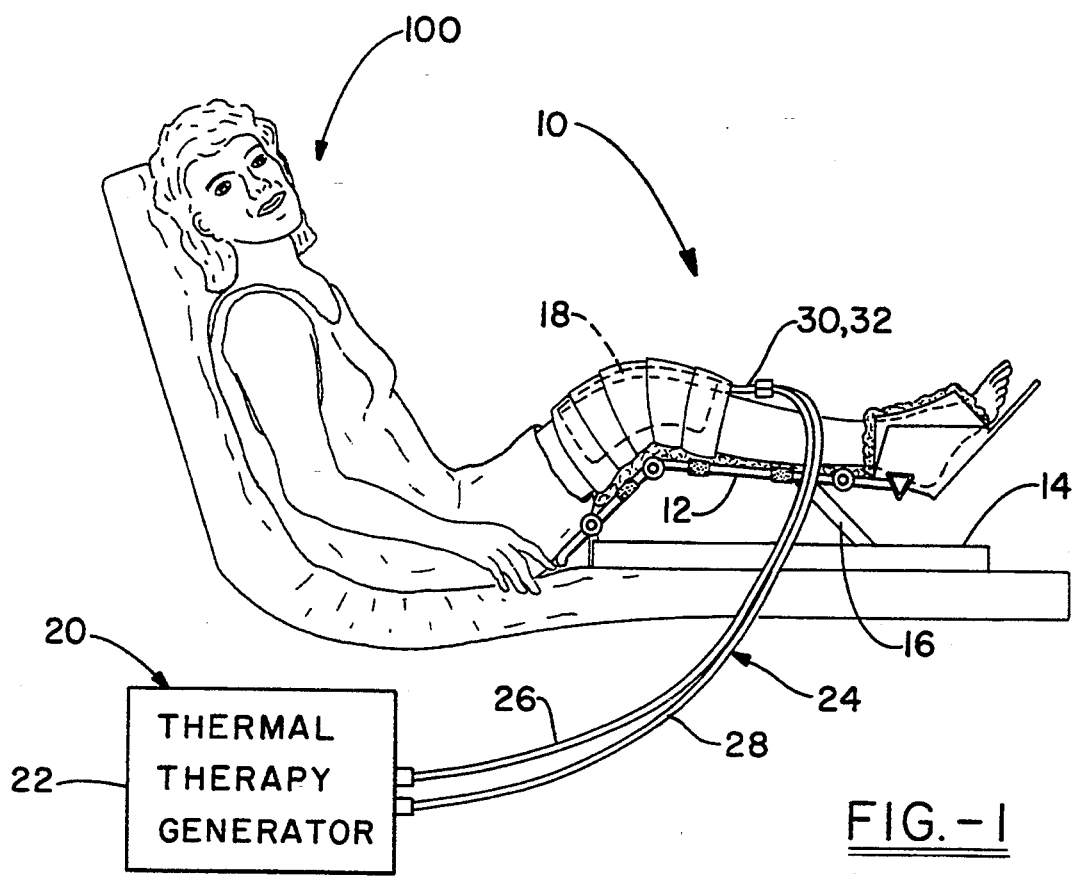
FIG. 1 is an illustration showing a patient undergoing CPM and thermal therapy.

FIG. 1 illustrates a patient 100 who has undergone knee surgery, and who is being treated by continuous passive motion ("CPM") therapy, as well as thermal therapy. The CPM therapy device, shown generally at 10, cradles the patient's knee, and passively raises and lowers the knee. The patent is simultaneously undergoing thermal therapy treatment.

The CPM device includes a cradle 12, and a base, 14. A drive mechanism 16, operates between the cradle and the base, to passively move the patient's limb. The patient is simultaneously undergoing thermal therapy treatment. The thermal therapy device, shown generally at 20, incorporates a thermal generating means such as thermoelectric modules contained within a housing 22, and fluid transfer means 24, which include an inlet conduit connection 26 and an outlet conduit connection 28. The fluid transfer means 24 are in fluid cooperation with a thermal transfer pad 18. In accordance with the present invention, the thermal transfer pad 18 has a soft flexible reinforced fluid inlet which provides for a greater area of fluid diffusion. The greater area of fluid diffusion inhibits blockage to fluid flows and facilitates simultaneous application of thermal therapy and CPM.

Figure 2:
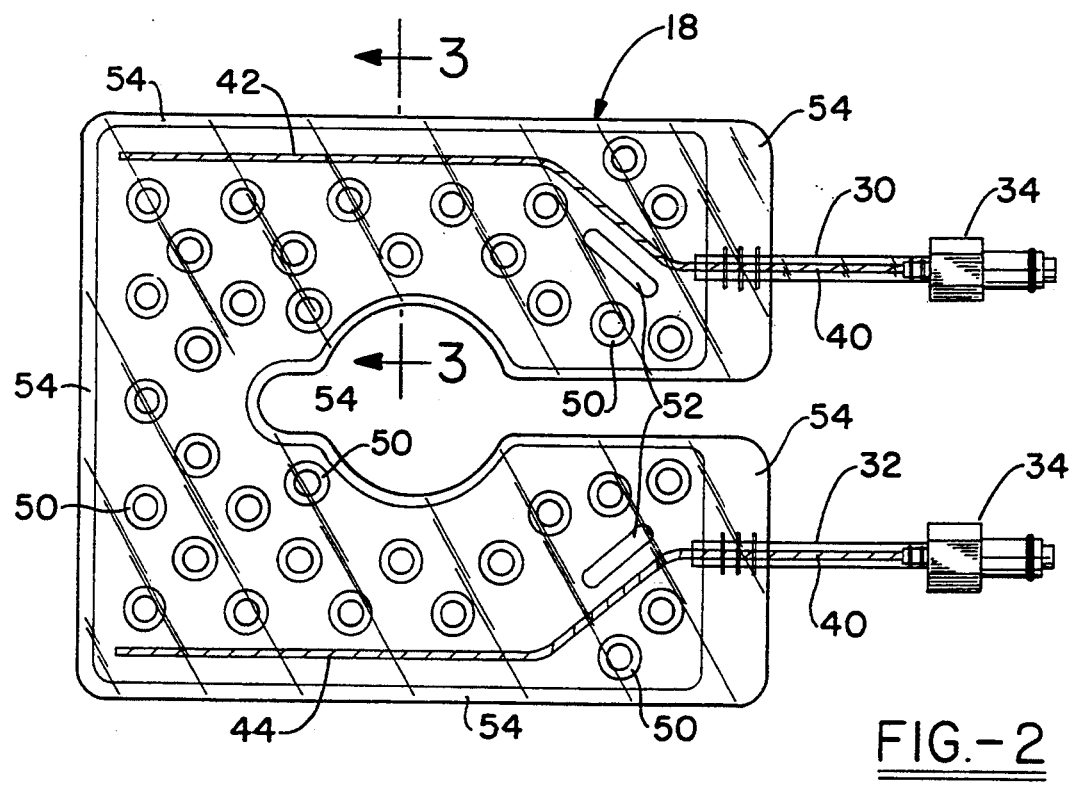
FIG. 2 is a plan view of a thermal transfer pad forming a primary element of the present invention.
Figure 3:
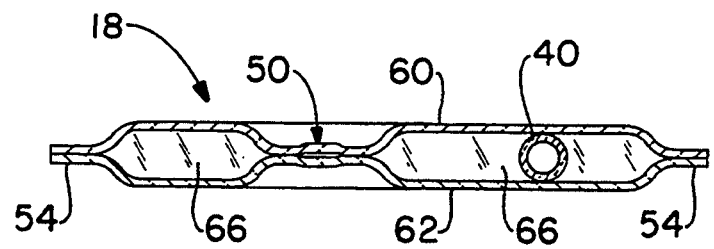
FIG. 3 is a greatly enlarged cross-sectional view through the thermal transfer pad shown in FIG. 2 as taken at line 3—3 thereof.
Figure 4:
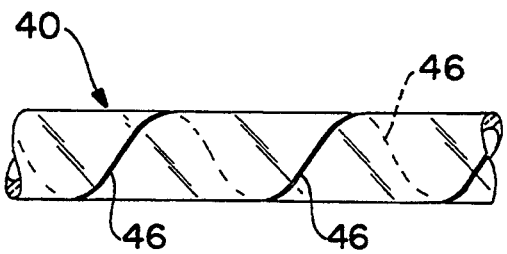
FIG. 4 is a greatly enlarged elevational view of a reinforcement conduit forming a part of the thermal transfer pad.

FIG. 2 illustrates a first embodiment of the thermal transfer pad of the present invention in which the fluid conduit reinforcement means comprises multiple concentric conduit sections. It should be understood, of course, that the reinforcement section could be incorporated into the external surfaces of the pad.

Figure 5:
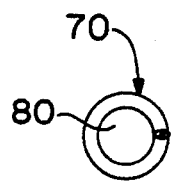
FIG. 5 comprising
Figure 5:
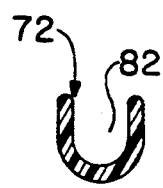
Figure 5:
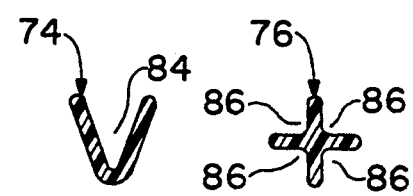
Figure 6:
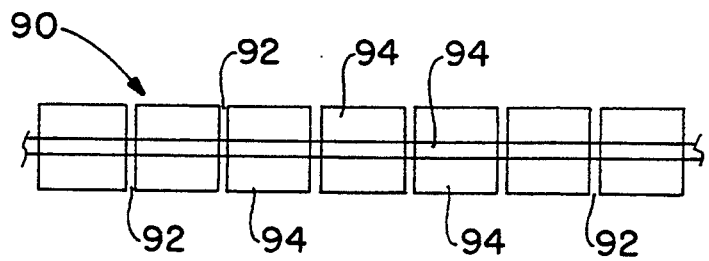
FIG. 6 is a side elevational view of an alternative to the one shown in FIG. 5D having a similar transverse cross-sectional shape.

Alternatively, as is shown in FIG. 5, the reinforcement section can include an internal conduit section 40 which extends in one direction beyond the pad 18 into the fluid transfer means 24, and in the other direction into the fluid transfer pad 18. Where the multi-conduit comprises reinforcements in the outer surfaces of the pad, the inlet conduit extends into the pad and comprises the internal conduit member. In such a case, it is preferable that the internal conduit includes an increased surface area of diffusion, such as provided by spiral cutting in the conduit, or an oblique angle of opening or even multiple holes in the walls of the conduit.

In the embodiment shown in FIG. 2, separate internal conduits 40 are provided. Preferably, there are two internal conduits 42, 44; one of which reinforces the inlet conduit 30 and one of which reinforces the outlet conduit 32.

The internal conduits 40 have an outer diameter which is smaller than the internal diameter of the inlet conduit 30 and of the outlet conduit 32. There is preferably a gap formed between the internal conduit reinforcement and the external inlet conduit, i.e., the internal reinforcement conduit 40 should have an outer diameter which is small enough so that the reinforcement is easily inserted into the outer tube. On the other hand, the reinforcement should be large enough to allow relatively unrestricted flow of the fluid through it. Further, the reinforcement tube 40 should be of a small enough outer diameter to avoid the possibility of pressure points on the patient where the transfer pad could leave marks on the patient, in particular, if the pad is applied with an elastic bandage. Thus, the internal conduit should have an outer diameter of from about 0.075 to about 0.45 inches, and preferably from about 0.1 to about 0.3 inches, and most preferably from about 0.1 to about 0.2 inches.

The outer tube 24 which forms the conduit connection to the pad, should also be large enough to maintain relatively unrestricted flow, and yet it should not be so large as to form a pressure point to the patient. It is preferable that the outer tube have an internal diameter of from about 0.15 to about 0.5, preferably from about 0.15 to about 0.4, and most preferably from about 0.2 to about 0.3 inches.

The wall thickness of the inlet and outlet conduits 30, 32 and of the reinforcement conduit 40 will depend somewhat on the properties of the material which is used to make them. The materials should be strong but flexible and have good low temperature characteristics. The outer conduit 30, for example, may have a wall thickness of from about 0.01 to about 0.2, and preferably from about 0.03 to about 0.1, while the internal reinforcement 30 should have a wall thickness of from about 0.01 to about 0.1 with a preferred range being from about 0.02 to about 0.07.

Internal conduit 40 may be made from any suitable material, including for example, polyethylene such as sold by Ark-plas Inc. or Alpha-Wire Corporation, having a Shore D hardness of from to 10 to 75; preferably 20 to 60, and the material should remain flexible between 40° F. and 125° F.

The internal conduit is a tube which is slit in a spiral about its longitudinal axis through the tube wall. The spiral is at a pitch of from about 0.5 revolutions per inch to about 40 revolutions per inch; and preferably 2 to about 20; and most preferably about 4 to about 12; with suitable examples being 5 revolutions and 8 revolutions. The internal conduit is illustrated as a slit tube, however, alternatively, the internal conduit may have an open spiral shape such as formed by a plastic coil. Metal coils or springs may be used but are inferior to the present invention since the internal conduit means should either be soft or devoid of sharp stiff edges in order to avoid piercing the top or bottom layer of the pad member.

The spiral cut is preferable to multiple holes in the walls of the internal conduit means since it is less likely to crimp and cause blockage to the fluid flow. It is preferable that the internal inlet conduit 31 extend a significant distance into the fluid transfer pad from the end of the inlet conduit, such as at least about two inches and optimally, the entire length of the pad. The distance that the internal conduit extends into the pad will depend, of course, upon the configuration of the pad and the desired flow pattern. It always desirable, that the conduit extend far enough to assure a uniform distribution and flow of the fluid throughout the entire pad member. This assures that the entire pad member will have a uniform thermal distribution.

The thermal transfer pad 18 further includes a pad member comprising a top membrane layer 60 which is sealed to a bottom membrane layer 62 to form an internal fluid pocket 66. Any suitable means may be used to seal the layers such as heat welding or adhesive sealing, preferably at the edges 54. It is further preferable that the internal pocket include baffles 50 so as to cause optimal fluid flow patterns within the thermal transfer pad. Elongate baffles 52 may be used to help maintain the position of the conduit 40. The baffles 50, can comprise transverse sections, or simply can comprise areas where the top layer of thermal transfer pad is adhered to the bottom layer of thermal transfer pad. The baffle can be created such as by the application of suitable adhesive, or more preferably, by heat welding, such as by RF welding. It is particularly preferable that the baffles are round such as shown in FIG. 2, since they have a maximum radius of curvature such as shown in FIG. 2, and therefore reduce the likelihood of electrical arcing if RF welding is used to make the baffles. The arcing increases the possibility of pad leakage under pressure.

Further as is shown in FIGS. 2 and. 4, the internal conduit means 40 includes a spiral cut 46 which passes entirely through the wall of the internal conduit means. Thus, the fluid may flow through the internal conduit means 40, or alternatively, if the conduit is subjected to a radial compressive force, the spiral cut opens along the longitudinal axis of the conduit in order to allow the fluid to escape. Thus, the transfer of the fluid media is assured at various locations along the longitudinal axis of the internal conduit means. Preferably, the internal conduit means is flexible and resilient, so that it returns to its shape when the compressive force is removed. The reinforcement conduit 40 of FIG. 2 is shown at 70 in FIG. 5A with a substantially round inner diameter 80.

The membranes, as well as the inner and outer conduit may be made of any impervious material suitable for medical applications, and preferably comprise a material which is sterilizable by gamma radiation such as for example, polyester, polyurethane, polyethylene, and polyvinyl chloride and silicon elastomers and the like. The membrane should have a thickness which is sufficient to impart sufficient strength to avoid rupture and to facilitate ease of construction and yet which is thin enough to provide for a high rate of thermal transfer and which has a high degree of flexibility. Suitable thicknesses are from about 0.003 to about 0.020 inch, preferably from about 0.005 to about 0.12 inch. A particularly preferred material remains flexible at suitable operating temperature, i.e., from about 40° F. to about 125° F. A particularly suitable product is polyether polyurethane or polyester polyurethane having a Shore A hardness of from about 70 to about 90 and sold by Deerfield Urethane Inc. or J.P.S. Elastomerics Corp. The pad may include further layers to facilitate thermal transfer, such as gel compositions or porous material. The fluid conduit means connecting the pad member with the thermal generating means are made from any suitable material such as previously discussed. Optimally, the conduit and membrane will be made from the same material.

The conduit means 24 are joined to the pad member by suitable means such as connectors 34 or by heat sealing the conduits in place. The fluid transfer conduits are preferably a material which may be compatible with the membrane material so as to form a heat seal joint. It is preferable that the membrane and conduit material is transparent so that it is possible to see the fluid.

Alternatively, as is shown in FIG. 5, the internal conduit means may comprise an open rather than a closed conduit, i.e., the conduit may include an open flow surface or channel. Such a surface 82 could be comprised of the internal surface of a two lobed, U-shaped conduit 72 or alternatively as shown in FIG. 5B, the surface 84 could be comprised of a V-shaped conduit 84. As a further embodiment, the reinforcement may have four lobes 76 or three lobes 78 so as to include multiple channels or flow surfaces 86, 88 such as are shown in FIGS. 5D and 5E. In one such example, the reinforcement 90 has four ribs 94, which form a cross-shaped cross-section with four flow channels. In order to maintain flexibility, the reinforcement of the ribs 94 includes periodic transverse slots 92. These slots could be spaced at 0.15 to 0.2 inch intervals, for example, and could vary in width from 0.005 to 0.05 inch.

While in accordance with the Patent Statutes, the best mode and preferred embodiment has been set forth, the scope of the invention is not limited thereto, but rather by the scope of the attached claims.

What is claimed is:

1. A fluid transfer pad comprising a first membrane in sealed cooperation with a second membrane to form a fluid receiving cavity and fluid conduit means comprising an inlet conduit and an outlet conduit, said inlet including a first end terminating in said fluid receiving cavity, and said transfer pad including a flexible internal conduit with walls having a substantially continuous spiral cut centered about the longitudinal axis of the conduit and extending within said inlet conduit beyond said first end into said fluid receiving cavity, said spiral cut internal conduit being free from edges which could rupture said first or second membrane.

2. The fluid transfer pad as set forth in claim 1, wherein said inlet conduit and said internal conduit are both comprised of a transparent material.

3. A fluid transfer pad comprising:
a first membrane having a first periphery and a second membrane having a second periphery, said first and second periphery being sealed to form a fluid receiving cavity, said first membrane and said second membrane each being made from a material which is sterilizable by gamma radiation and having a Shore A hardness of from about 70 to about 90 and having a thickness of from about 0.3 to about 0.020 mils;
a fluid conduit means comprising an inlet conduit and an outlet conduit made from a material having a Shore A hardness of from about 70 to about 90 having an internal diameter of from about 0.15 to about 0.5 inches, and having a wall thickness of from about 0.15 to about 0.2 inches, said inlet including a first end terminating in said fluid receiving cavity; and said conduit means further comprising at least one flexible internal conduit extending from within said fluid conduit means into said fluid receiving cavity, said flexible internal conduit being a tube having an outer diameter of about 0.075 to about 0.45 inches, a Shore A hardness of from about 70 to about 90, and including a longitudinal axis, said tube having tube walls with a thickness of from about 0.15 to about 0.2 inches, and including a slit through said tube walls spiraling at a pitch of from about ½ to about 40 revolutions per inch.

* * * * *